United States Patent [19]

Farr

[11] Patent Number: 5,112,345
[45] Date of Patent: May 12, 1992

[54] ATHERECTOMY CUTTER WITH ARCUATE BLADES

[75] Inventor: Andrew F. Farr, Spring Valley, Calif.

[73] Assignee: InterVentional Technologies, San Diego, Calif.

[21] Appl. No.: 628,397

[22] Filed: Dec. 17, 1990

[51] Int. Cl.[5] ............................................. A61B 17/32
[52] U.S. Cl. .................................... 606/159; 606/180; 604/22
[58] Field of Search .............. 606/159, 167, 170, 180, 606/106; 604/22; 128/757, 754, 758; 15/104.1 R, 104.12, 104.33; 30/316

[56] References Cited

U.S. PATENT DOCUMENTS

| 775,679 | 11/1904 | Nowotny | 15/104.12 |
|---|---|---|---|
| 2,292,713 | 8/1942 | O'Leary | 15/104.33 |
| 2,670,537 | 3/1954 | Campbell | 30/316 |
| 3,449,783 | 6/1969 | Kirchke | 15/104.12 |
| 3,605,725 | 9/1971 | Bentov | 128/2.05 R |
| 3,882,877 | 5/1975 | Douvas et al. | 606/170 |
| 3,990,453 | 11/1976 | Douvas et al. | 128/305 |
| 4,589,412 | 5/1986 | Kensey | 128/305 |
| 4,631,052 | 12/1986 | Kensey | 604/22 |
| 4,664,112 | 5/1987 | Kensey et al. | 128/341 |
| 4,685,458 | 8/1987 | Lackrone | 606/159 |
| 4,690,140 | 9/1987 | Mecca | 128/305 |
| 4,696,667 | 9/1987 | Masch | 604/22 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,842,579 | 6/1989 | Shiber | 604/22 |
| 4,857,045 | 8/1989 | Rydell | 604/22 |
| 4,886,061 | 12/1989 | Fischell et al. | 604/22 |
| 4,966,604 | 10/1990 | Reiss | 604/22 |

Primary Examiner—C. Fred Rosenbaum
Assistant Examiner—William W. Lewis
Attorney, Agent, or Firm—Nydegger & Associates

[57] ABSTRACT

An over-the-wire atherectomy cutter includes a hollow cylindrical sleeve which is coaxially attached at its proximal end to a hollow rotatable catheter. The periphery of the distal end of the sleeve is sharpened.

A hollow, substantially cylindrical body is coaxially positioned within the sleeve in an interference fit. A frustum-shaped portion is formed on the distal end of the body and tapers inwardly toward a hollow cylindrical distal tip. The frustum-shaped portion has two openings which extend the axial length of the frustum-shaped portion, to create a pair of straight blades that connect the body to the tip. The straight blades are contiguous to the sharpened distal end of the sleeve to establish a pair of diametrically opposed arcuate cutting edges that are positioned on the distal end of sleeve.

5 Claims, 1 Drawing Sheet

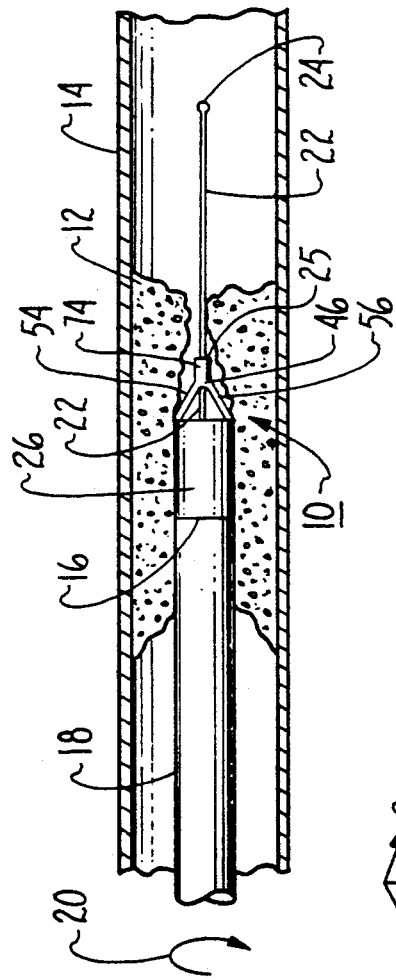

ATHERECTOMY CUTTER WITH ARCUATE BLADES

FIELD OF THE INVENTION

The present invention relates generally to devices which remove stenoses from blood vessels. More particularly, the present invention relates to atherectomy devices. The present invention particularly, though not exclusively, relates to cutting elements for atherectomy devices which cut a relatively smooth bore through atherosclerotic plaque.

BACKGROUND OF THE PERTINENT TECHNOLOGY

Blockages of arteries in human beings is unfortunately a widespread malady. As is well known, blockages or reduced blood flow through the coronary arteries to the heart can cause heart attacks, while blockages or reduced blood flow through the arteries to the brain can cause strokes. Similarly, arterial blockage or reduced blood flow through arteries to other parts of the body can result in grave consequences to the affected organ or limb.

The build up of atherosclerotic plaque is a chief cause of arterial blockages and reduced arterial blood flow. Not surprisingly, several methods have been introduced to alleviate the effects of plaque build up. One such method is the procedure known as angioplasty, which uses an inflatable device to compact and break up arterial stenoses. One typical angioplasty device is disclosed in U.S. Pat. No. 4,896,669 to Bhate, et al. The Bhate, et al. angioplasty device includes an inflatable balloon which is inserted while in its deflated state into an artery. The balloon is attached to one end of a hollow catheter, and the opposite end of the catheter is attached to a fluid source. Thus, the balloon can be inflated by infusing fluid from the fluid source into the balloon through the catheter.

To treat an arterial stenosis, the Bhate, et al. balloon is guided through the artery over a wire to position the balloon next to the stenosis, and the balloon is then inflated with fluid. As the balloon expands, the plaque which comprises the stenosis is compacted and broken up. The balloon is then deflated and removed from the artery.

While effective for breaking up stenoses, angioplasty devices such as the Bhate, et al. device discussed above do not remove the plaque from the artery. Consequently, the pieces of plaque can still disrupt blood flow or enter the blood stream. In either case they can cause future blockages in blood vessels. Fortunately, a procedure known as atherectomy has been devised which both clears the stenoses and then removes the pieces of the plaque which comprised the stenosis from the blood vessel. The technique of plaque removal by atherectomy typically includes inserting a guide wire into the affected artery and then advancing a hollow cutting device over the wire until the cutting device is positioned adjacent the stenosis (i.e., area of plaque build up) in the artery. Then, the cutting device is further advanced into the stenosis to cut a channel through the plaque, thereby increasing blood flow through the artery. Cut pieces of plaque can then be removed from the blood stream by drawing the pieces into the hollow cutting device.

Not surprisingly, a large number of atherectomy devices have been introduced. One such device is disclosed in U.S. Pat. No. 4,895,166 to Farr et al. which is assigned to the same assignee as the present invention. The Farr et al. device includes a frustum-shaped cutter which is attached to the distal end of a hollow catheter and is positioned into the artery over a guide wire. According to the Farr et al. disclosure, the cutter has two openings that define two straight cutting blades. As the cutter is advanced into the stenosis, the cutter is rotated to cut plaque. Excised plaque which enters the openings of the cutter is subsequently removed through the hollow catheter.

While the Farr et al. device is effective for its intended purpose, it happens that a helically-shaped uncut ridge of plaque can occasionally be left on the arterial wall as a rotating cutter advances through the stenosis. This ridge of plaque, along with fibers of plaque which extend from the ridge, can cause the clotting of blood adjacent the ridge and can perhaps lead to a restenosis of the affected artery. Accordingly, the present invention recognizes a need to provide an atherectomy device which cuts a channel through a stenosis, the channel having a smooth bore which is substantially free of plaque ridges and fibers.

It is therefore an object of the present invention to provide an atherectomy cutter that can cut a channel through a stenosis in an artery or a blood vessel of a living being. Another object of the present invention is to provide an atherectomy cutter which can be guided over a guide wire to the arterial stenosis to be removed. Yet another object of the present invention is to provide an atherectomy cutter that cuts a channel having a relatively smooth bore through an arterial stenosis. Finally, it is an object of the present invention to provide an atherectomy cutter which is relatively easy to use and cost-effective to manufacture.

SUMMARY OF THE INVENTION

An over-the-wire atherectomy cutting device includes a rotatable catheter which is attached at its distal end to a cutter. The cutter has two coplanar arcuate blades, each of which is contiguous with a straight blade that extends away from the plane of the arcuate blades. Accordingly, the cutter has two cutting elements, with each element including a straight blade and an arcuate blade.

More specifically, the cutter of the present invention includes a hollow cylindrical sleeve which has a distal end and a proximal end. The proximal end of the sleeve is attached to the rotatable catheter, and the circular periphery of the distal end of the sleeve is sharpened. A hollow, substantially cylindrical body is coaxially positioned within the sleeve, in an interference fit, and a frustum-shaped portion extends from the distal end of the body and tapers inwardly away from the body toward a hollow cylindrical distal tip. In accordance with the present invention, the frustum-shaped portion has two openings, which extend the axial length of the frustum-shaped portion to create a pair of blades that connect the body with the tip. Thus, each opening in the frustum-shaped portion is partially defined by the axially-extending edges of the blades. For the present invention, one edge of each opening is sharpened to establish a straight cutting edge.

In accordance with the present invention, the body is positioned within the sleeve such that the proximal ends of the straight cutting blades are contiguous to the sharpened periphery of the distal end of the sleeve.

Consequently, one straight blade, together with the arcuate portion of the periphery of the sleeve which extends between the cutting edge of the straight blade and the next straight blade, establishes a cutting element. In other words, each sharpened portion of the periphery of the sleeve that is between the two straight blades defines a respective arcuate cutting blade. Thus, each arcuate blade extends between the sharpened leading edge of a first straight blade and the unsharpened following edge of a second straight blade.

The novel features of this invention, as well as the invention itself, both as to its structure and its operation, will be best understood from the accompanying drawing, taken in conjunction with the accompanying description, in which similar reference characters refer to similar parts, and in which:

BRIEF DESCRIPTION OF THE DRAWINGS

FIG. 1 is a schematic view of the novel atherectomy cutter of the present invention in its intended environment;

FIG. 2 is a perspective view of the novel atherectomy cutter of the present invention;

FIG. 3 is a cross-sectional view of the novel atherectomy cutter of the present invention, as seen along the line 3—3 in FIG. 2; and FIG. 4 is a cross-sectional view of the novel atherectomy cutter of the present invention, as seen along the line 4—4 in FIG. 2.

DESCRIPTION OF THE PREFERRED EMBODIMENT

Referring initially to FIG. 1, an atherectomy cutter, generally designated 10, is shown cutting a substantially smooth bore through a stenosis 12 which has formed on the interior wall of an artery 14. As shown, cutter 10 is attached at its proximal end 16 to a hollow rotatable catheter 18. Cutter 10 is hollow, and is coaxially attached to hollow catheter 18. Catheter 18 is any suitable device which can transmit torque (e.g., in the direction indicated by arrow 20) from a motor (not shown) to device 10.

FIG. 1 also shows that cutter 10 can be steered to stenotic lesion 12 within artery 14 over a flexible guide wire 22. As shown, guide wire 22 extends through torque tube 18 and atherectomy cutter 10. Also, guide wire 22 can include a protuberance 24 which is formed on the distal end of guide wire 22. The diameter of protuberance 24 is larger than the diameter of distal end 25. Consequently, protuberance 24 prevents the withdrawal of guide wire 22 from atherectomy cutter 10.

It is to be understood that the materials of atherectomy cutter 10 are preferably lightweight and strong, as well as chemically inert vis-a-vis the body tissue of artery 14. For example, atherectomy cutter 10 can be made of 400 series stainless steel. Similarly, guide wire 22 can be a flexible yet strong stainless steel wire which is suitable for use as an atherectomy guide wire.

The details of atherectomy cutter 10 are best seen in cross-reference to FIGS. 2, 3, and 4. FIG. 2 shows that cutter 10 includes an outer sleeve 26 which surrounds an inner body 28. More particularly, as shown in cross-reference to FIGS. 2 and 3, sleeve 26 and body 28 are both hollow and substantially cylindrical in shape, with body 28 being positioned within sleeve 26 in an interference fit. If desired, body 28 can be epoxy-bonded or spot welded as at weld 30 (shown in FIGS. 3 and 4) to sleeve 26. Alternatively, body 28 can be formed integrally with sleeve 26, e.g. by forging or casting body 28 with sleeve 26 in accordance with common metallurgical principles.

FIG. 2 also shows that the distal periphery 32 of sleeve 26 is sharp to form two arcuate cutting blades 34 and 36 which can be diametrically opposed. More specifically, distal periphery 32 of sleeve 26 is tapered inwardly from the outer wall 38 of sleeve 26 to the inner wall 40 of sleeve 26, as best seen in FIGS. 3 and 4. As shown in FIG. 2, arcuate cutting blades 34 and 36 are accordingly formed with respective arcuate cutting edges 42 and 44.

Still referring to FIG. 2, a hollow portion 46 which is shaped as a right circular conical frustum is shown integrally formed with body 28. As shown, this frustum-shaped portion 46 extends distally from body 28, with the proximal end 47 of frustum-shaped portion 46 being juxtaposed with distal periphery 32 of sleeve 26. Also, frustum-shaped portion 46 is formed with two openings 48 and 50, through which material (e.g., excised plaque) may pass into the interior lumen 52 (shown in FIG. 3) of portion 46.

As shown best in FIG. 2, the openings 48 and 50 establish straight diametrically opposed cutting blades 54 and 56. In accordance with the disclosure above, the respective proximal ends 58, 60 of the straight blades 54, 56 are formed integrally with proximal end 47 of frustum-shaped portion 46, and are therefore juxtaposed with periphery 32 of sleeve 26. Also, each straight blade 54, 56 is formed with a sharpened leading edge and a following edge. More particularly, in reference to FIG. 2, when atherectomy cutter 10 is to be rotated in the direction indicated by arrow 62, edge 64 will be the leading edge of blade 54, while edge 66 will be the following edge of blade 54. Accordingly, edge 64 will be sharpened to form a straight cutting edge on blade 54. Also, when atherectomy cutter 10 is to be rotated in the direction indicated by arrow 62, edge 68 of blade 56 will be the leading edge of blade 56 and edge 70 of blade 56 will be the following edge of blade 56. Accordingly, edge 68 will be sharpened to form a straight cutting edge on blade 56. It is to be understood that cutter 10 can be rotated in the direction opposite the direction indicated by arrow 62, in which case edges 66, 70 will be sharpened.

As shown in FIGS. 2 and 3, the straight blades 54 and 56 are angled inwardly toward the axis 72 of atherectomy cutter 10 from body 28 to a hollow cylindrical distal tip 74. Stated differently, the straight blades 54 and 56 are oriented relative to axis 72 with the distance between respective distal ends 76, 78 of blades 54, 56 and axis 72 being less than the distance between axis 72 and respective proximal ends 58, 60 of blades 54, 56. Thus, the diameter D1 of tip 74, shown in FIG. 3, is less than the diameter D2 of body 28. Furthermore, FIG. 2 shows that the blades 54, 56 are respectively attached to or integrally formed with proximally-projecting extensions 80, 82 of tip 74. As shown, tip 74 is distanced from body 28 and is oriented coaxially with body 28. Thus, tip 74, frustum-shaped portion 46, body 28, and sleeve 26 share a common axis 72. Also, it will be appreciated from the disclosure above that the respective lumens of hollow tip 74, hollow frustum-shaped portion 46, and hollow body 28 are in fluid communication with the lumen of torque tube 18, shown in FIG. 1.

As can readily be appreciated with reference to FIGS. 2 and 3, distal periphery 32 of sleeve 26 lies in a plane which is substantially perpendicular to axis 72 of atherectomy cutter 10. Thus, arcuate cutting edges 42, 44 of respective arcuate cutting blades 34, 36 also lie in a plane which is substantially perpendicular to axis 72. Furthermore, as can be appreciated with reference to FIG. 2, arcuate cutting edge 42 of arcuate blade 34 extends between the proximal end of straight cutting edge 64 of straight blade 54 and the proximal end of following edge 70 of straight blade 56. Additionally, arcuate cutting edge 44 of arcuate blade 36 extends between the proximal end of straight cutting edge 68 of straight blade 56 and the proximal end of following edge 66 of straight blade 54. Stated differently, each of the straight blades 54 and 56 extends distally from periphery 32 between successive arcuate blades 34 and 36. Thus, straight cutting blade 54 and arcuate cutting blade 34, which is contiguous to straight blade 54, form a first cutting element. Also, straight cutting blade 56 and arcuate cutting blade 36, which is contiguous to straight blade 56, form a second cutting element.

OPERATION

In the operation of atherectomy cutter 10, reference is initially made to FIG. 1. In accordance with well-known surgical techniques, guide wire 22 is positioned within artery 14. Then, catheter 18 with atherectomy cutter 10 is advanced over wire 22 until cutter 10 is positioned adjacent stenosis 12. Catheter 18 is then rotated, which consequently causes cutter 10 to rotate.

As cutter 10 is rotated, cutter 10 is advanced into stenosis 12 to cut a substantially smooth bore through stenosis 12. More particularly, straight blades 54 and 56 cut a channel in stenosis 12 as cutter 10 is advanced into stenosis 12. Because straight blades 54 and 56 are angled inward distally, blades 54 and 56 penetrate as they cut through stenosis 12 which extends from the side walls into the lumen of the artery. Plaque which is excised by blades 54 and 56 enters the lumen 52 of cutter 46 through openings 48 and 50, and is subsequently drawn through cutter 46 by applying a vacuum to the lumen of catheter 18.

Depending on their rate of advance into the stenosis 12, as straight blades 54 and 56 cut a channel through the stenosis 12 they can leave behind helical ridges and fibers of plaque which project into the cut channel. These ridges and fibers of plaque, however, are cut by arcuate blades 34 and 36 as blades 34 and 36 are advanced through the channel of stenosis 12. In other words, arcuate blades 34 and 36 cut the helical plaque ridges and fibers which can otherwise remain within the cut channel of stenosis 12 after the passage therethrough of straight blades 54 and 56. Plaque which is excised by arcuate blades 34 and 36 enters the lumen 52 of frustum-shaped portion 46 through openings 48 and 50, and can subsequently be drawn out of frustum-shaped portion 46 by applying a vacuum to the lumen of catheter 18.

While the particular atherectomy cutter with arcuate blades as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An atherectomy cutter which comprises:
   a hollow cylindrical sleeve defining a longitudinal axis and having a sharpened distal edge;
   a pair of straight blades each said straight blade extending distally from said distal edge of said sleeve and angled from said distal edge toward said axis to establish a pair of arcuate blades, on said distal edge between said straight blades; and
   a hollow cylindrical body having a proximal end and a distal end, said straight blades being attached to said distal end of said body, said body being held within said sleeve an interference fit therewith.

2. An atherectomy cutter as recited in claim 1 wherein said sleeve has a first diameter, and said cutter further comprises a hollow cylindrical tip having a second diameter smaller than said first diameter, said tip having a proximal end attached to said straight blades, said tip being coaxial with said sleeve.

3. An atherectomy cutter as recited in claim 1 wherein said straight blades are diametrically opposed.

4. An atherectomy cutter as recited in claim 1 wherein said arcuate blades are diametrically opposed.

5. An atherectomy cutter as recited in claim 1 wherein said sleeve has a proximal end and said cutter further includes an elongated hollow catheter attached to said proximal end of said sleeve, said catheter defining a lumen, said lumen being in fluid communication with the lumen of said hollow sleeve.

* * * * *